United States Patent
Metzger et al.

(10) Patent No.: US 8,834,573 B2
(45) Date of Patent: Sep. 16, 2014

(54) PYROCARBON ORTHOPEDIC IMPLANT

(75) Inventors: Robert Metzger, Wakarusa, IN (US); Kevin T. Stone, Winona Lake, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 394 days.

(21) Appl. No.: 13/399,129

(22) Filed: Feb. 17, 2012

(65) Prior Publication Data

US 2012/0150307 A1    Jun. 14, 2012

Related U.S. Application Data (63) Continuation of application No. 12/502,642, filed on Jul. 14, 2009, now Pat. No. 8,123,813.

(51) Int. Cl.
*A61F 2/38* (2006.01)
*A61F 2/30* (2006.01)

(52) U.S. Cl.
CPC .......... *A61F 2/38* (2013.01); *A61F 2310/00574* (2013.01); *A61F 2002/30337* (2013.01); *A61F 2310/00023* (2013.01); *A61F 2002/3895* (2013.01); *A61F 2310/00161* (2013.01); *A61F 2310/00017* (2013.01); *A61F 2/389* (2013.01); *A61F 2310/00029* (2013.01); *A61F 2002/30934* (2013.01); *A61F 2002/30981* (2013.01); *A61F 2/3859* (2013.01)
USPC .................. 623/20.14; 623/20.15; 623/18.11

(58) Field of Classification Search
CPC . A61F 2/38; A61F 2/385; A61F 2002/30024; A61F 2002/30934; A61F 2002/3863
USPC ........... 623/18.11, 20.14, 20.15, 20.21, 20.23
See application file for complete search history.

(56) References Cited

U.S. PATENT DOCUMENTS

| | | | |
|---|---|---|---|
| 3,521,302 A | 7/1970 | Müller | |
| 3,938,198 A | 2/1976 | Kahn et al. | |
| 4,101,985 A | 7/1978 | Baumann et al. | |
| 4,224,699 A | 9/1980 | Weber | |
| 4,454,612 A | 6/1984 | McDaniel et al. | |
| 4,491,987 A | 1/1985 | Park | |
| 4,904,534 A | 2/1990 | Nagai | |
| 5,037,445 A | 8/1991 | Sander et al. | |
| 5,123,927 A | 6/1992 | Duncan et al. | |
| 5,163,960 A | 11/1992 | Bonutti | |
| 5,171,282 A * | 12/1992 | Pequignot | 623/20.35 |
| 5,181,926 A | 1/1993 | Koch et al. | |
| 5,197,987 A | 3/1993 | Koch et al. | |
| 5,314,492 A | 5/1994 | Hamilton et al. | |

(Continued)

OTHER PUBLICATIONS

Kerluke, D.R., et al. X-Ray Processing of Advanced Composites at 5 MeV and Above. (May 12-16, 2002) presented at 47th International SAMPE Symposium and Exhibition. Society for the Advancement of Material and Process Engineering, vol. 47, Book 1 of 2 Books, pp. 600-606.

(Continued)

*Primary Examiner* — Bruce E Snow
(74) *Attorney, Agent, or Firm* — Harness, Dickey (57) ABSTRACT

An orthopedic prosthetic device having at least one pyrocarbon insert is provided. The prosthetic device can include a prosthetic component having an articulating surface and a bone engagement surface. The articulating surface can be formed of a material that is distinct from pyrocarbon and is arranged to receive the at least one pyrocarbon insert so as to position a pyrocarbon articulating surface of the at least one pyrocarbon insert relative to the prosthetic component articulating surface.

22 Claims, 8 Drawing Sheets

(56) References Cited

U.S. PATENT DOCUMENTS

| | | | |
|---|---|---|---|
| 5,443,512 A | 8/1995 | Parr et al. |
| 5,458,647 A | 10/1995 | Brochier et al. |
| 5,480,449 A | 1/1996 | Hamilton et al. |
| 5,534,033 A | 7/1996 | Simpson |
| 5,549,700 A | 8/1996 | Graham et al. |
| 5,593,445 A | 1/1997 | Waits |
| 6,090,145 A | 7/2000 | Hassler et al. |
| 6,146,423 A | 11/2000 | Cohen et al. |
| 6,414,086 B1 | 7/2002 | Wang et al. |
| 6,436,146 B1 | 8/2002 | Hassler et al. |
| 6,566,451 B2 | 5/2003 | Wang et al. |
| 6,638,069 B2 | 10/2003 | Hagenbuch et al. |
| 6,786,930 B2 | 9/2004 | Biscup |
| 6,905,511 B2 | 6/2005 | Wang et al. |
| 8,123,813 B2 | 2/2012 | Metzger et al. |
| 2003/0069605 A1 | 4/2003 | Bonutti et al. |
| 2003/0144741 A1 | 7/2003 | King et al. |
| 2003/0144742 A1 | 7/2003 | King et al. |
| 2004/0068320 A1 | 4/2004 | Robie et al. |
| 2005/0119757 A1 | 6/2005 | Hassler et al. |
| 2005/0146070 A1 | 7/2005 | Muratoglu et al. |
| 2005/0167893 A1 | 8/2005 | Wang et al. |
| 2005/0246032 A1 | 11/2005 | Bokros et al. |
| 2006/0235542 A1 | 10/2006 | Hodorek et al. |
| 2008/0288081 A1 | 11/2008 | Scrafton et al. |
| 2011/0015740 A1 | 1/2011 | Metzger et al. |

OTHER PUBLICATIONS

Kerluke, David R., et al. "Electron Beam Processing for Automotive Composite Applications." (2002) pp. 1-5.

* cited by examiner

PYROCARBON ORTHOPEDIC IMPLANT

CROSS-REFERENCE TO RELATED APPLICATIONS

This application is a continuation of U.S. patent application Ser. No. 12/502,642 filed on Jul. 14, 2009 now U.S. Pat. No. 8,123,813, the entire disclosure of which is incorporated herein by reference.

FIELD

The present disclosure relates generally to a prosthetic device having a pyrocarbon insert.

BACKGROUND

The statements in this section merely provide background information related to the present disclosure and may not constitute prior art.

It is generally known in the art to provide prosthetic implants for replacing various human anatomical parts that have become damaged due to wear or injury. These implants are produced from a biocompatible material and interact with adjacent body portions to replicate anatomical movement.

Often, implants are used to replace articulating and/or bearing anatomical features such as the ball joint portion of the femur and the bearing portion of the tibia. Most often, the portions of the implant that will undergo the greatest stresses and loads are formed of metals due to their known strength and longevity. Metal structures, however, can have a higher modulus of elasticity than bone.

SUMMARY

This section provides a general summary of the disclosure, and is not a comprehensive disclosure of its full scope or all of its features.

In one form an orthopedic prosthetic device having at least one pyrocarbon insert is provided. The at least one pyrocarbon insert can have a pyrocarbon articulating surface. The prosthetic device can include a prosthetic component having a bone engaging surface and an articulating surface. The articulating surface can be formed of a material that is distinct from pyrocarbon and is arranged to receive the at least one pyrocarbon insert so as to position the articulating surface of the at least one pyrocarbon insert relative to the prosthetic component articulating surface.

In another form a method for forming a prosthetic component is provided. The method can include forming a pyrocarbon insert having a pyrocarbon coating formed over an insert substrate material, and determining if there is any excess pyrocarbon deposited onto the formed pyrocarbon insert. The method can also include shaping an exterior of the formed pyrocarbon insert if it is determined that there is excess pyrocarbon. The pyrocarbon insert can be secured to an articulating surface of the prosthetic device such that the pyrocarbon insert is positioned in a congruent or a proud position relative to the articulating surface.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features. Although the following description can be related generally to a prosthetic device having pyrocarbon inserts at an articulating surface of the device for use in a prepared portion of the anatomy, such as an exemplary knee joint prosthesis, it will be understood that the prosthetic device having pyrocarbon inserts at the articulating surface, as described and claimed herein, can be used in any appropriate prosthetic joint. Therefore, it will be understood that the following discussions are not intended to limit the scope of the appended claims.

Figures 1A, 1B:
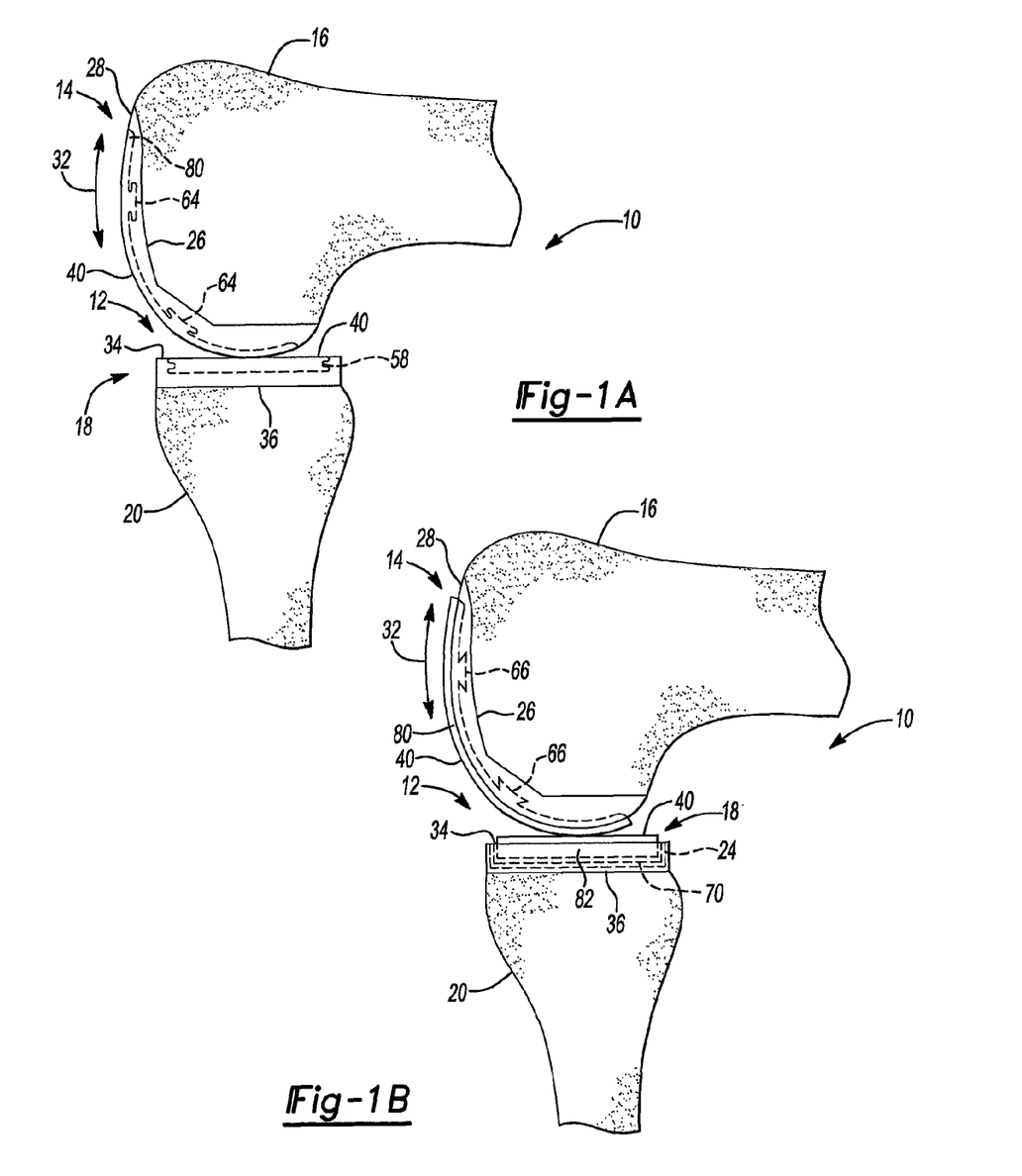
FIGS. 1A and 1B are medial views of an exemplary knee joint prosthesis having pyrocarbon inserts according to the principles of the present disclosure.

With general reference to FIG. 1A, an exemplary prosthetic device 10 for a knee joint having at least one pryocrabon insert 12 is shown. The exemplary prosthetic device 10 can include a unicondylar femoral component 14 for implantation in a femur 16 and a tibial component 18 for implantation in a tibia 20. While prosthetic device 10 is shown as having a unicondylar femoral component 14 and a corresponding tibial component 18, it should be understood that the at least one pyrocarbon insert 12 can be applied to various other types of prostheses including, but not limited to, a total knee joint prosthesis, a hip joint prosthesis, and a shoulder joint prosthesis.

The femoral component 14 can be formed of a biocompatible material suitable for implantation in an anatomy, such as stainless steel, titanium or cobalt chromium. The tibial component 18 can likewise be formed of a suitable metal material for implantation in an anatomy as well as can also include a bearing insert 24 that can be formed of a biocompatible polymer material such as polyethylene or polyaryletheretherketone (PEEK). Tibial component 18 can also be formed solely from the polymer material. The femoral component 14 can include a bone engagement surface 26 and an articulating surface 28 positioned generally opposite of bone engagement surface 26. Articulating surface 28 generally articulates in a direction 32 about a bearing surface 34 of tibial component 18. Bearing surface 34 can be positioned generally opposite of a bone engagement surface 36 of tibial component 18. Femoral component 14 with the at least one pyrocarbon insert 12 can also articulate about cartilage or bone when a tibial component is not implanted. Similarly, femur 16 can also articulate about tibial component 18 with the at least one pyrocarbon insert 12 when a femoral component is not implanted.

The at least one pyrocarbon insert 12 can be formed using a chemical vapor deposition process where pyrocarbon is deposited onto a suitable core or substrate, such as a graphite substrate. The at least one pyrocarbon insert 12 can be formed using any suitable biocompatible pyrocarbon material. The chemical vapor deposition process can be carried out in a fluidized bed furnace heated to over 1200 degrees Celsius where a silicon gas carrier and hydrocarbon are fed into the furnace for the deposition process. The deposition process can result in a pyrolytic carbon or pyrocarbon coating over the graphite substrate that has mechanical properties similar to those of graphite and diamond, with very good biocompatibility, a low coefficient of friction, and high wear resistance. For example, the pyrocarbon inserts have a higher wear resistance and lower coefficient of friction than that of stainless steel, titanium, cobalt chromium, ceramic and polyethylene, and can thereby provide a longer life, higher wear resistant articulating surface material.

Pyrocarbon inserts formed on the graphite substrate can also provide the advantage of having physical properties that closely match those of bone. More specifically, in addition to the above-mentioned high wear resistance and low coefficient of friction, the pyrocarbon inserts can also have a modulus of elasticity relatively equal to that of cortical bone which can serve to provide a relatively even stress transfer between the pyrocarbon insert and the bone. On the other hand, common metal and polymer materials for prosthetic components can have a modulus of elasticity higher or lower than bone which can provide a potential for uneven stress transfer from the implant to the corresponding bone.

Turning now to FIGS. 8A-8K, features that can be included with the at least one pyrocarbon insert 12 will be discussed in greater detail with reference to an exemplary tibial pyrocarbon insert 12'. Pyrocarbon insert 12' can include a bearing or articulating surface 40, a bottom surface 42, and a sidewall 44 as generally shown in FIGS. 8A-8D. Pyrocarbon insert 12' can be formed in a variety of shapes including an elongated oval shape 48, a circular shape 50, an elongated oval shape with a varying width 52, and a rectangular shape 53, as generally shown in FIGS. 8A-8D. It should be appreciated that the above shapes are merely exemplary of the various shapes and widths into which pyrocarbon insert 12' can be formed.

Figure 8A:
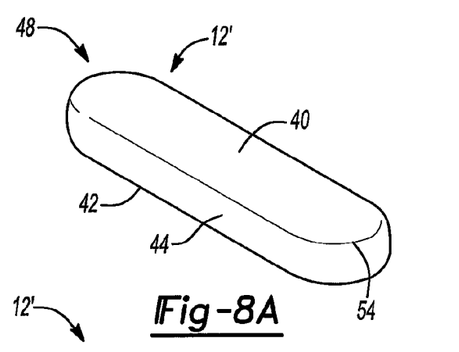
FIGS. 8A-8D are perspective views of exemplary shapes of the pyrocarbon inserts according to the principles of the present disclosure.
Figure 8B:
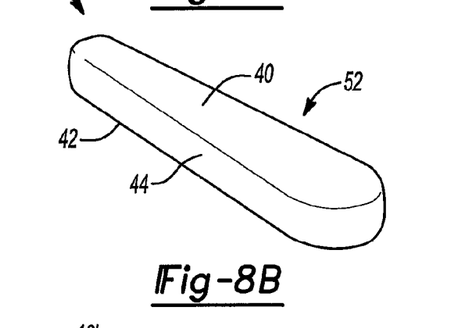
Figure 8C:
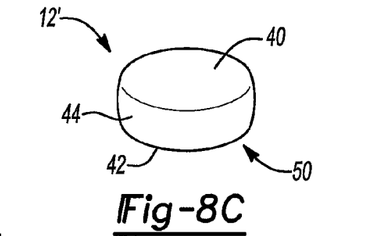
Figure 8D:
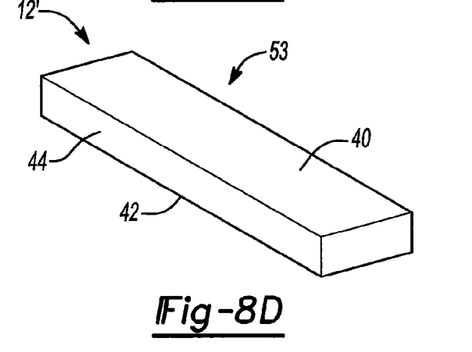
Figure 8E:
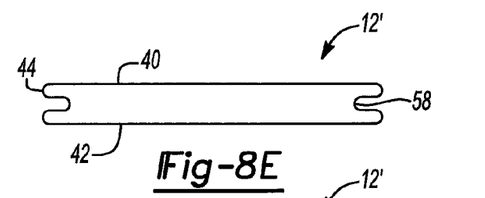
FIGS. 8E-8K are side views of exemplary attachment arrangements of the pyrocarbon inserts according to the principles of the present disclosure.
Figure 8F:
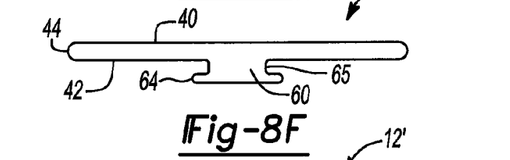
Figure 8G:
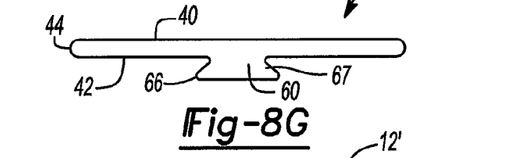
Figure 8H:
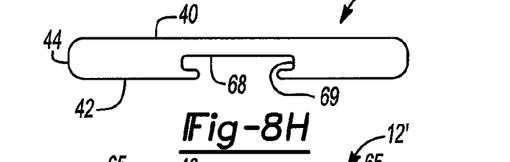
Figure 8I:
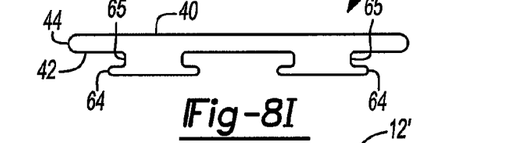
Figure 8J:
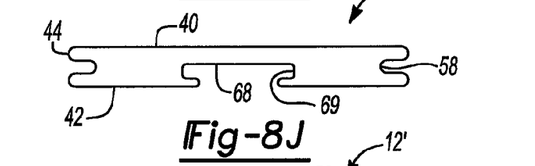
Figure 8K:
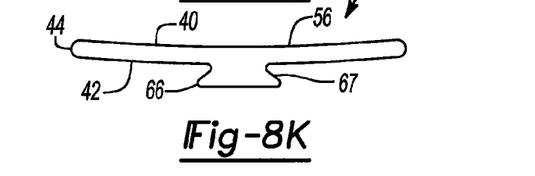

Pyrocarbon insert 12' can also include rounded or smooth edges 54 as a result of the pyrocarbon coating formed over the graphite substrate as discussed above. As shown in FIG. 8K, bearing or articulating surface 40 can also include an arcuate shape 56 that conforms to the geometry of the articulating or bearing surface of the receiving prosthetic device, such as the femoral or tibial components 14, 18 of exemplary prosthetic device 10. The pyrocarbon insert 12' can be formed to have a thickness of generally 3 mm, which does not include the thickness of any associated attachment portions, as will be discussed. While a thickness of 3 mm for pyrocarbon insert 12' is discussed, it should be appreciated that the thickness of pyrocarbon insert 12' can be varied as may be required for certain prosthetic device applications.

The pyrocarbon insert 12' can be configured to be secured to a respective prosthetic device, such as femoral and/or tibial components 14, 18, using a mechanical coupling arrangement or an adhesive arrangement. The mechanical coupling arrangement can be used when the pyrocarbon insert 12' is to be molded or cast into place in the respective prosthetic device. With the high melting point of pyrocarbon insert 12', the pyrocarbon insert 12' can be molded or cast into place in a prosthetic component formed with either the metallic or nonmetallic materials discussed above.

For the mold or cast in place applications, pyrocarbon insert 12' can include various mechanical coupling arrangements that can be selected based on numerous criteria such as the desired geometry of the pyrocarbon insert and the prosthetic device that will be receiving the pyrocarbon insert. The mechanical coupling mechanisms can be engaged by the molten material used to form the respective prosthetic component during the molding or casting processes to secure the pyrocarbon inserts in a desired position to the articulating surface. For example, pyrocarbon insert 12' can include an annular groove or recess 58 positioned in a sidewall 44 that is arranged to receive the prosthetic component material during the mold or cast in place operation so as to permanently secure the pyrocarbon insert to the articulating surface as shown in FIG. 8E. Pyrocarbon insert 12' can also include a protruding stem portion 60 extending from bottom surface 42. Stem portion 60 and can include various attachment configurations including an annular projection 64 forming a recess 65 and a dovetail configuration 66 forming a recess 67 as shown in FIGS. 8F and 8G. Pyrocarbon insert 12' can also include an undercut 68 forming a recess 69 in the bottom surface 42 as shown in FIG. 8H, as well as a combination of mechanical coupling arrangements as shown, for example, in FIGS. 8I and 8J.

For applications where the pyrocarbon insert 12' can be adhered to a recess 70 in the respective articulating or bearing surface, an adhesive such as cyanoacrylate can be used to bond pyrocarbon insert 12' to the recess. While cyanoacrylate is disclosed for securing the pyrocarbon insert, it should be understood that any appropriate adhesive can be used to secure the pyrocarbon insert to the articulating or bearing surface. Due to the nature of the pyrocarbon insert forming process, exterior dimensions of the pyrocarbon insert may vary slightly from one pyrocarbon insert to another. To accommodate for this potential dimensional variation, the pyrocarbon insert 12' can be machined to a specific exterior dimension or shape 53 that corresponds to an interior dimension or shape of the recess 70 arranged to receive the machined pyrocarbon insert 12' (See FIGS. 1B and 8D).

Using pyrocarbon inserts in the exemplary prosthetic device 10 can provide the advantage of the physical and material properties of pyrocarbon while also balancing the high cost associated with prosthetic implants formed entirely of pyrocarbon. As will be discussed below, the at least one pyrocarbon insert 12 can be positioned in a component or components of a prosthetic device having the various shapes and attachment configurations discussed with respect to exemplary insert 12'. The at least one pyrocarbon insert 12 can also be positioned in various alignment configurations with respect to the direction of articulation 32 as will also be discussed below.

With reference to FIGS. 1A-3, the at least one pyrocarbon insert 12 can include a plurality of inserts 80 embedded or nested in femoral component 14 during a molding or casting operation such that articulating surface 40 is flush with articulating surface 28 and the at least one pyrocarbon insert is surrounded by the articulating surface material. The plurality of pyrocarbon inserts can be secured in place by having the articulating surface material engage the exemplary annular projection 64 and recess 65 of stem portion 60 during a molding or casting operation that can be used to form femoral component 14. The plurality of inserts 80 can have the elongated oval shape 48 and can be positioned generally parallel to the direction of articulation 32 as shown, for example in FIG. 2, where a longitudinal centerline 74 of each insert 80 is parallel to the direction of articulation 32.

Figure 2:
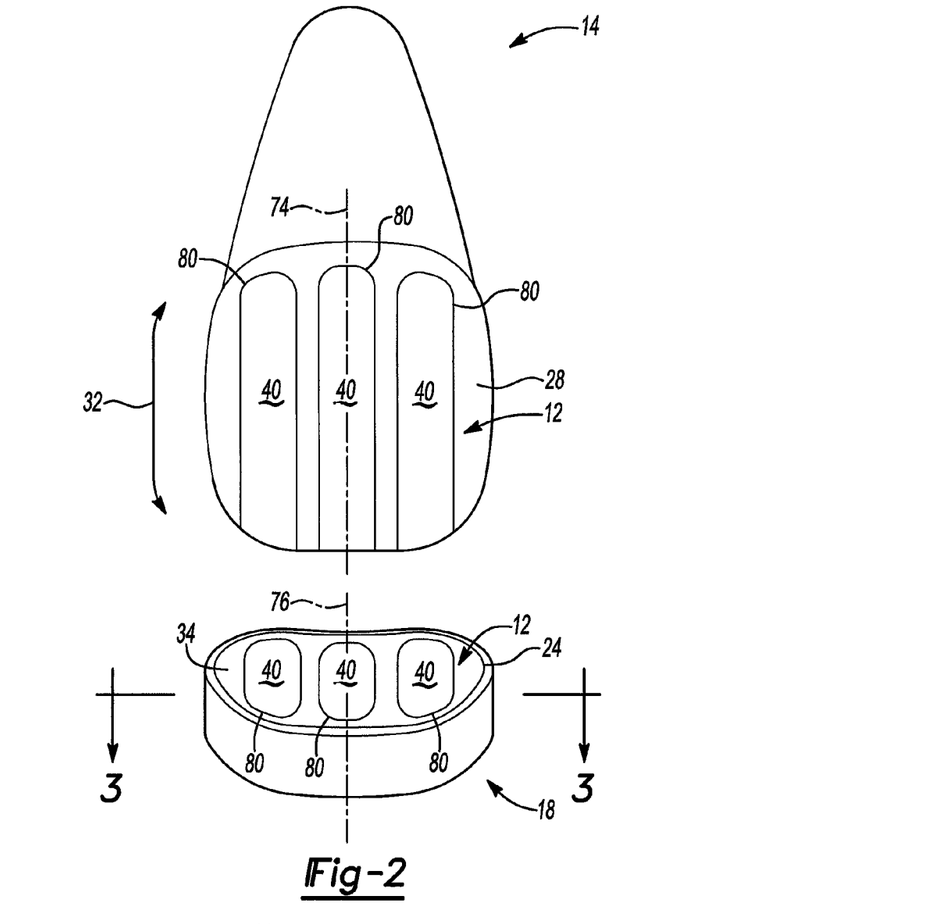
FIG. 2 is a partial perspective view of exemplary femoral and tibial components having pyrocarbon inserts according to the principles of the present disclosure.
Figure 3:
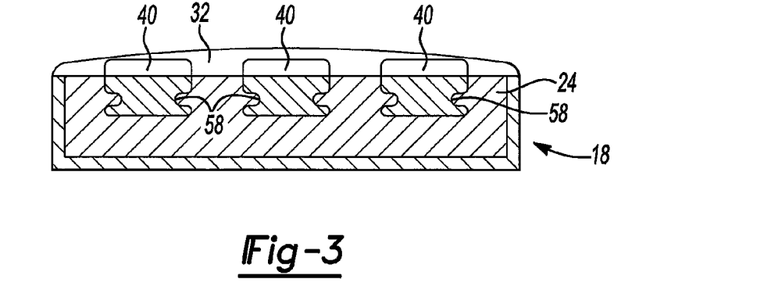
FIG. 3 is a sectional view taken along line 3-3 of FIG. 2 according to the principles of the present disclosure.
Figures 4A, 4B:
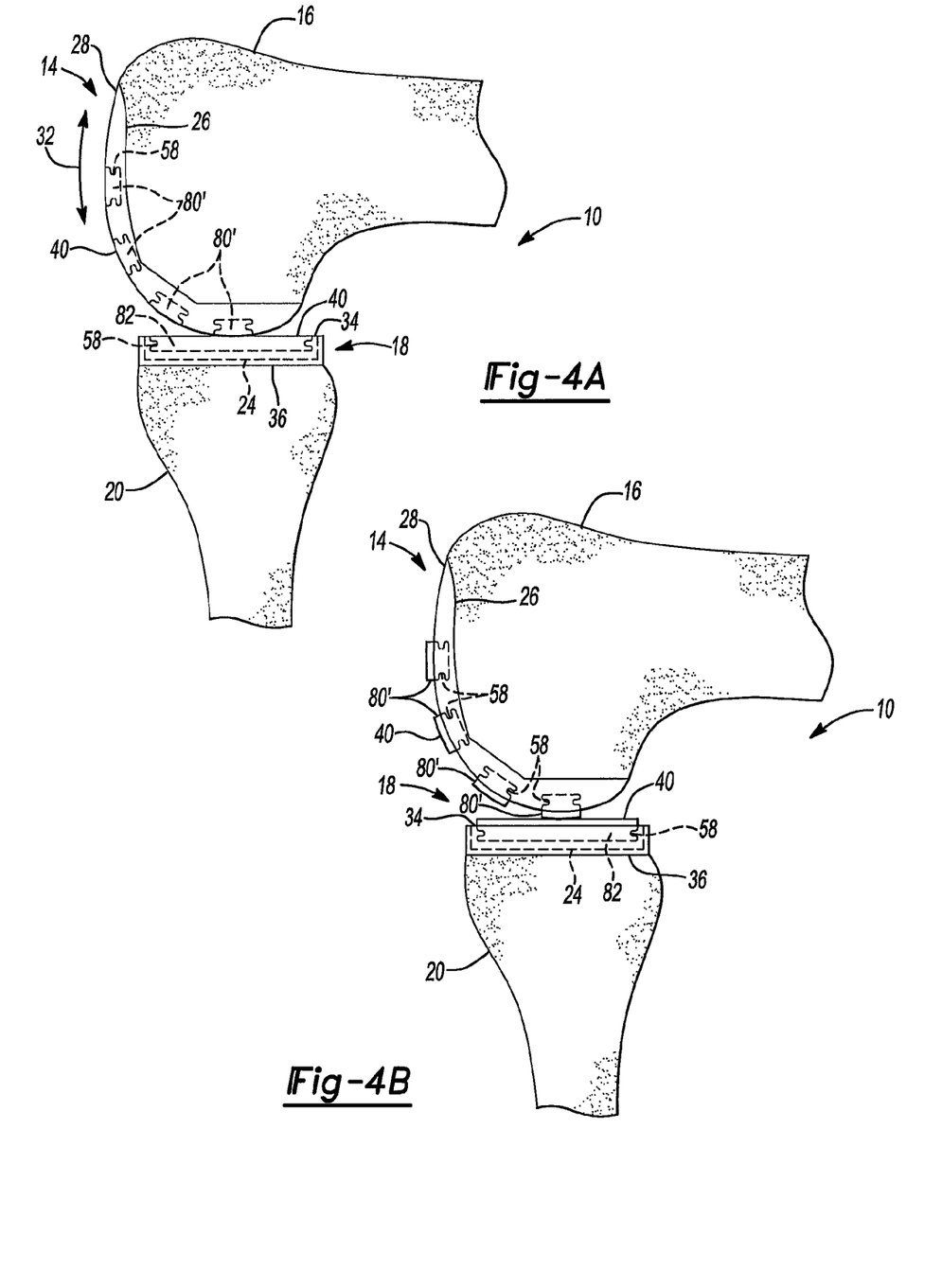
FIGS. 4A and 4B are medial views of the exemplary knee joint prosthesis having pyrocarbon inserts according to the principles of the present disclosure.
Figures 5A, 5B, 6:
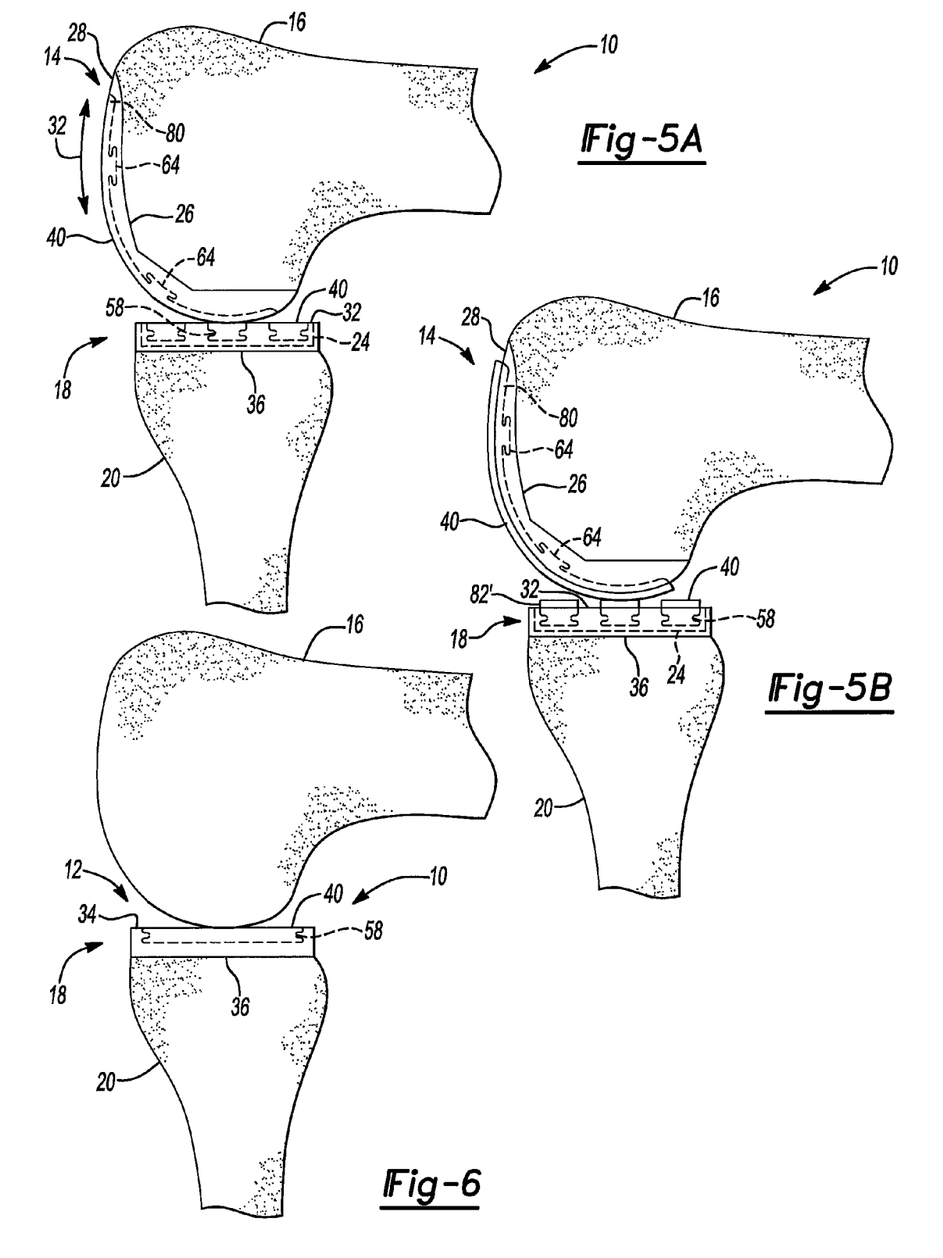
FIGS. 5A and 5B are medial views of the exemplary knee joint prosthesis having pyrocarbon inserts according to the principles of the present disclosure.
FIG. 6 is a medial view of an exemplary knee joint prosthesis having pyrocarbon inserts according to the principles of the present disclosure.

Tibial component 18 can likewise include a corresponding plurality of pyrocarbon inserts 82 also configured such that articulating surface 40 is flush with bearing surface 34. Pyrocarbon inserts 82 can also be aligned with the inserts 80 such that longitudinal centerline 74 aligns with a longitudinal centerline 76 of pyrocarbon inserts 82. In this manner, pyrocarbon inserts 80 and 82 can be in articulating engagement with each other once the femoral and tibial components 14, 18 are implanted, as generally shown in FIGS. 1A and 2. Pyrocarbon inserts 82 can also be secured to the tibial component during a molding or casting operation where the bearing surface material engages the annular undercut or recess 58 in sidewall 44.

The plurality of pyrocarbon inserts 80 can also be embedded in femoral component 14 so as to extend above or be proud of articulating surface 28 as shown in FIG. 1B. Tibial component 18 can include polymer bearing insert 24 having a recess or recesses 70 arranged to receive pyrocarbon inserts 80 having the machined or formed shape 53. The plurality of inserts 82 can be secured to recesses 70 with the adhesive and be positioned so as to be proud of the bearing surface 34 as also shown in FIG. 1B. Pyrocarbon inserts 80, 82 can also be positioned in additional configurations where only one of the respective pyrocarbon inserts 80, 82 is proud of its respective articulating or bearing surface. For example, pyrocarbon inserts 80 can be positioned proud of articulating surface 28 and pyrocarbon inserts 82 can be positioned flush or congruent with bearing surface 34, or vice-versa. It should be appreciated that articulating surface 28 and bearing surface 34 can articulate against a mating structure when the at least one pyrocarbon insert 12 is positioned flush with the respective surfaces 28, 34, and may not articulate against a mating structure when the at least one pyrocarbon insert 12 is positioned proud of surfaces 28, 34 so as to extend above surfaces 28, 34.

Figure 7A:
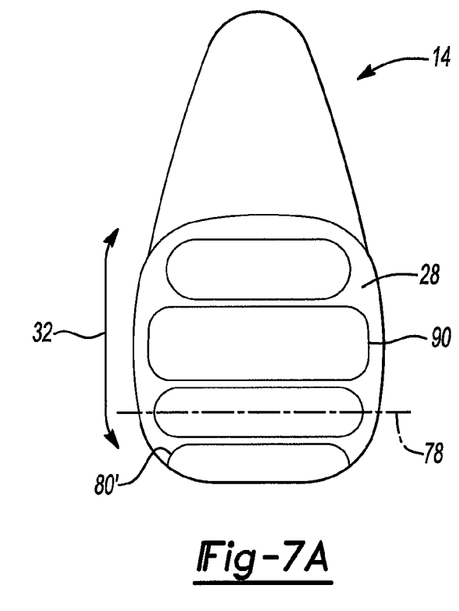
FIGS. 7A-7D are partial perspective views of the exemplary femoral component having pyrocarbon inserts according to the principles of the present disclosure.
Figure 7B:
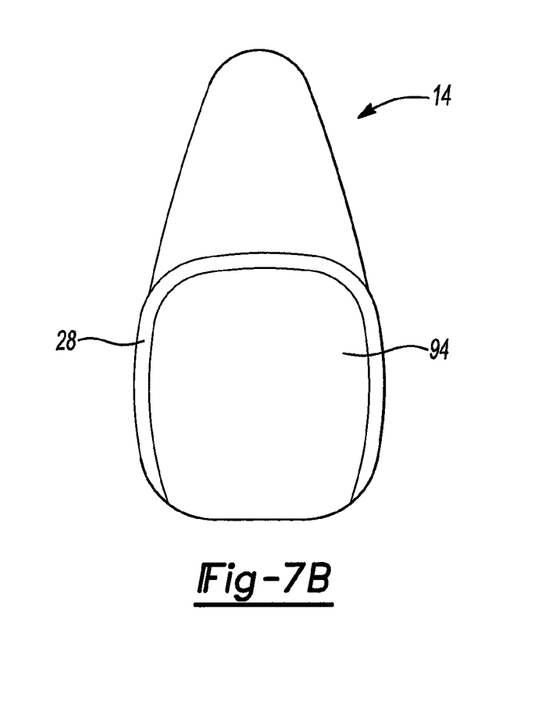

With additional reference to FIGS. 4A-5B, femoral component 14 can include a plurality of pyrocarbon inserts 80' positioned so as to be flush or proud of articulating surface 28 and generally perpendicular to the direction of articulation 32 such that a longitudinal centerline 78 of each pyrocarbon insert 80' is perpendicular to the direction of articulation 32 (FIG. 7A). Similarly, tibial component 18 can include a plurality of pyrocarbon inserts 82' positioned so as to be flush or proud of bearing surface 34 and generally perpendicular to the direction of articulation 32.

Pyrocarbon inserts 80, 80', 82, 82' can also be configured in various additional combinations as may be desired for certain prosthetic device applications. For example, femoral component 14 can include pyrocarbon inserts 80' positioned flush or proud of articulating surface 28 and tibial component 18 can include pyrocarbon inserts 82 positioned flush or proud of bearing surface 34. Femoral component 14 can alternatively include pyrocarbon inserts 80 positioned either flush or proud of articulating surface 28 and tibial component 18 can include a pyrocarbon inserts 82' positioned either flush or proud of bearing surface 34.

In addition, it should be understood that the pyrocarbon inserts 12 can also be positioned in only one of the prosthetic components of a multi-component prosthetic device, such as exemplary prosthetic device 10. For example and with additional reference to FIG. 6, exemplary tibial component 18 having pyrocarbon inserts 12 is shown in articulating engagement directly with femur 16 that does not have a femoral implant. It should also be appreciated that femur 16 can alternatively include femoral component 14 with pyrocarbon inserts 12 and be in articulating engagement directly with tibia 20. Thus, a prosthetic implant, such as femoral component 14 with pyrocarbon inserts 12, can engage and articulate about bone, cartilage, or another implant device with or without pyrocarbon inserts.

With reference to FIGS. 7A-7D, the at least one pyrocarbon insert 12 can include various other shapes and configurations that can be molded, cast or adhered in place to femoral an/or tibial components 14, 18, as may be desired for various prosthetic device applications. For example, certain of the pyrocarbon inserts 80, 80', 82, 82' can include a larger width 90 as shown in FIG. 7A. The at least one pyrocarbon insert 12 can also include a single pyrocarbon insert 94 that covers a substantial amount of the articulating and/or bearing surfaces 28, 34, as shown, for example, in FIG. 7B with reference to femoral component 14. In addition, the femoral and/or tibial components 14, 18 can include a plurality of pyrocarbon inserts 98 having circular shape 50 and arranged in a mosaic pattern as shown with femoral component 14 in FIG. 7D.

Figure 7C:
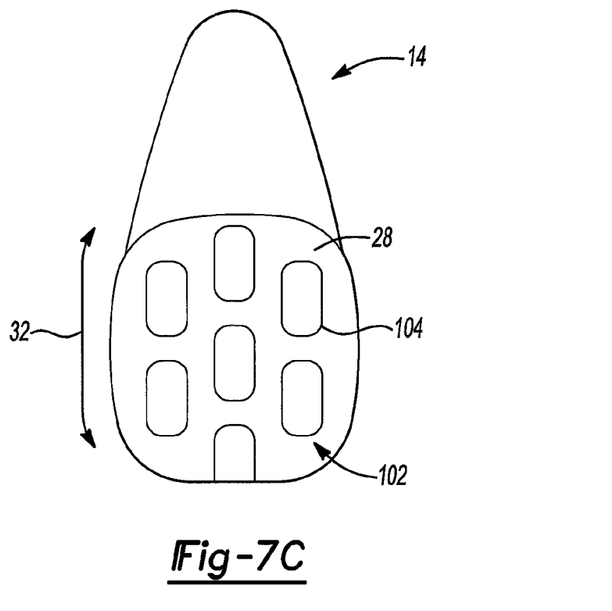
Figure 7D:
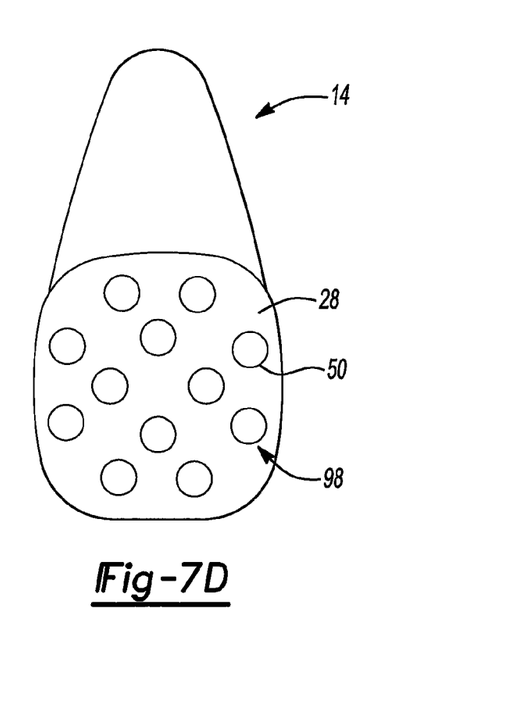

As yet another example, the femoral and/or tibial components 14, 18 can include a plurality of pyrocarbon inserts 102 having an oval shape 104 as shown with femoral component 14 in FIG. 7C. The pyrocarbon inserts 102 with shape 104 can be positioned in a mosaic pattern while being aligned in a direction perpendicular or parallel to the direction of articulation 32. Further, it should be appreciated that pyrocarbon inserts 98 and 102 can be used in various combinations with pyrocarbon inserts 80, 80', 82, 82' either in the same prosthetic component, such as femoral component 14, or in a mating component, such as tibial component 18. The at least one pyrocarbon insert 12 can also be configured in any one of the shapes and configurations discussed above to cover approximately 30-90 percent of the articulating or bearings surfaces 28, 34, respectively.

Figures 9, 10:
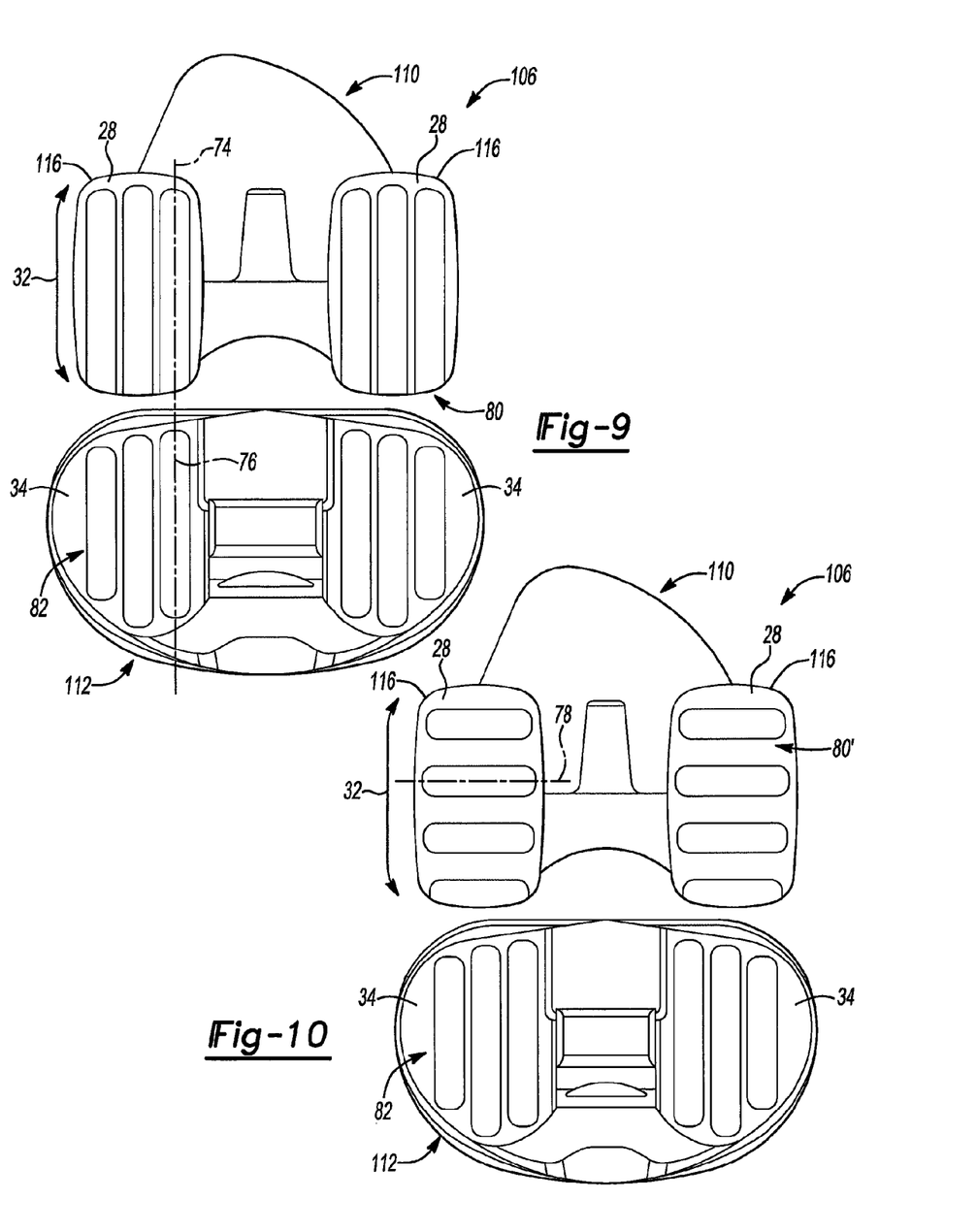
FIG. 9 is a partial perspective view of an exemplary alternative femoral component and tibial component having pyrocarbon inserts according to the principles of the present disclosure.
FIG. 10 is a partial perspective view of the exemplary alternative femoral and tibial components having pyrocarbon inserts according to the principles of the present disclosure.

Referring now to FIGS. 9-10, another exemplary prosthetic device 106 for a knee joint is shown and can include a femoral component 110 and a tibial component 112. The femoral component 110 can include a pair of condyles 116 with articulating surfaces 28 and the tibial component can include a corresponding pair of bearing surfaces 34. Femoral component 110 can include pyrocarbon inserts 80 positioned on each of condyles 116 so as to be flush or proud of articulating surface 28 as discussed above with reference to exemplary prosthetic device 10. Tibial component 112 can include bearing surfaces 34 formed integral with or on top of a tibial tray. Tibial component 112 can also include corresponding pyrocarbon inserts 82 positioned in bearing surfaces 34 so as to align with the plurality of inserts 80 as shown in FIG. 9. The plurality of inserts 82 can also be positioned in tibial component 112 so as to be flush or proud of bearing surface 34. Femoral component 110 can also include pyrocarbon inserts 80' positioned generally perpendicular to the direction of articulation 32 as shown in FIG. 10. It should also be appreciated that exemplary prosthetic device 106 can include similar combinations of the inserts 80, 80', 82, 82', 98 and 102 as discussed above with reference to exemplary prosthetic device 10.

Figure 11:
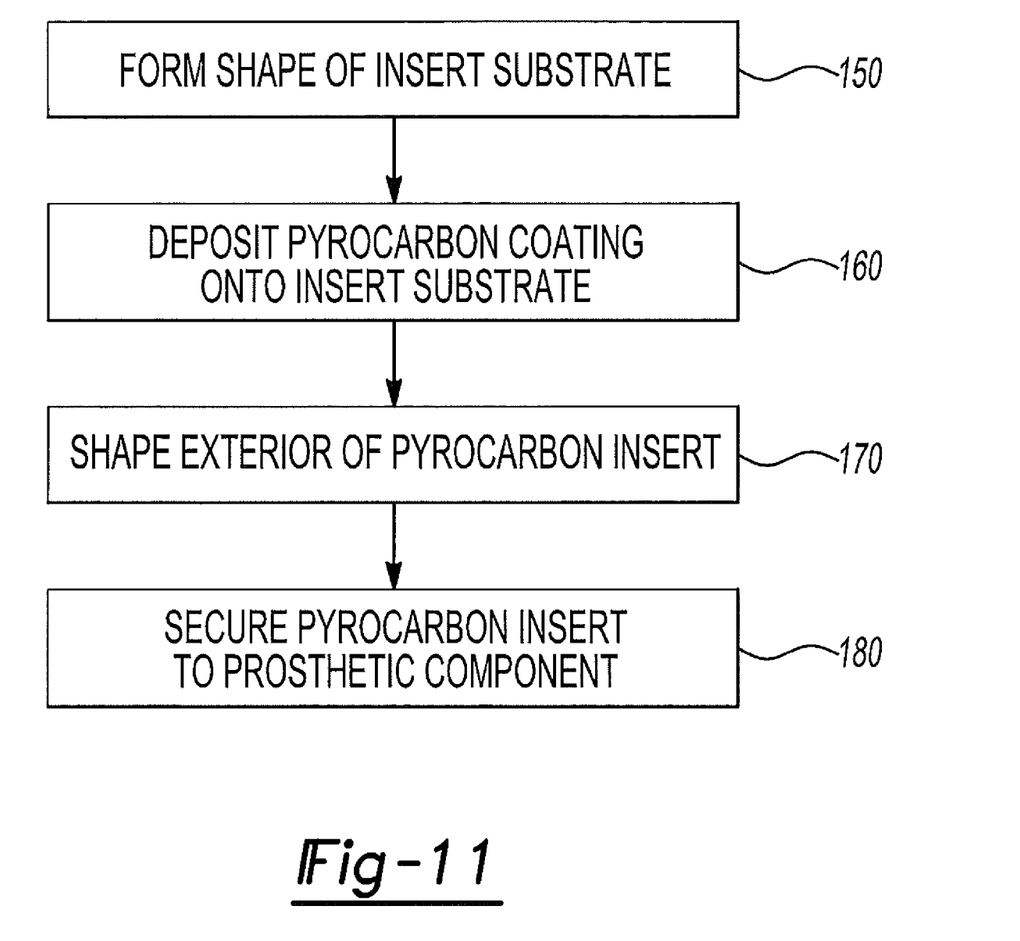
FIG. 11 is a flowchart illustrating a method according to the principles of the present disclosure.

Referring now to FIG. 11, various steps that may be involved in forming a prosthetic device, such as devices 10 and/or 106 with components having pyrocarbon inserts 12, are shown according to the teachings of the present disclosure. Initially, the graphite substrate can be formed into a desired shape at 150 and can then coated with pyrocarbon at 160 using the chemical vapor deposition process discussed above. Once coated with pyrocarbon, the in-process pyrocarbon insert can then be prepared to be secured to the prosthetic component at 170. The preparation can include determining if the in-process insert will be molded or cast in place in the articulating surface material or adhered to a recess formed in the articulating surface. If the in-process pyrocarbon insert is to be molded or cast into place, the mechanical coupling arrangement may need to be machined or shaped to remove any excess pyrocarbon that may have built-up during the deposition process. If the in-process pyrocarbon insert is to be adhered to the recess, then the in-process insert may need to be shaped or machined such that exterior dimensions of the insert substantially correspond to interior dimensions of the recess. Once the preparation at 170 is either completed or determined not to be required, the in-process pyrocarbon insert is now in the form of pyrocarbon insert 12 and can be secured to the respective prosthetic component at 180. As discussed above, pyrocarbon insert 12 can be secured to a prosthetic component through a molding or casting operation where insert 12 is molded or cast in place, or secured to the prosthetic component using an appropriate adhesive.

While specific examples have been described in the specification and illustrated in the drawings, it will be understood by those of ordinary skill in the art that various changes can be made and equivalents can be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example can be incorporated into another example as appropriate, unless described otherwise, above. Moreover, many modifications can be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this invention, but that the scope of the present disclosure will include any embodiments falling within the foregoing description and the appended claims.

What is claimed is:

1. An orthopedic prosthetic device, comprising:
a first plurality of pyrocarbon inserts each having a first pyrocarbon articulating surface and an elongated body defining a first longitudinal axis;
a second plurality of pyrocarbon inserts each having a second articulating surface and an elongated body defining a second longitudinal axis;
a first prosthetic component having a first bone engaging surface and an articulating surface, said articulating surface being formed of a material distinct from pyrocarbon and arranged to receive said first plurality of pyrocarbon inserts so as to position the first pyrocarbon articulating surfaces relative to the articulating surface, the first plurality of pyrocarbon inserts surrounded by the articulating surface; and
a second prosthetic component having a second bone engaging surface and an articular surface, said articular surface being formed of a material distinct from pyrocarbon and arranged to receive said second plurality of pyrocarbon inserts so as to position the second pyrocarbon articulating surfaces relative to the articular surface, the second plurality of pyrocarbon inserts surrounded by the articular surface, the first and second pyrocarbon articulating surfaces configured to cooperate with each other;
wherein the first and second prosthetic components comprise a direction of articulation, the first longitudinal axis of each of the first plurality of pyrocarbon inserts being parallel to the direction of articulation and the second longitudinal axis of each of the second plurality of pyrocarbon inserts being parallel to the direction of articulation, each of the first plurality of pyrocarbon inserts being aligned with a respective one of the second plurality of pyrocarbon inserts.

2. The prosthetic device of claim 1, wherein said first pyrocarbon articulating surfaces are positioned flush with said first prosthetic component articulating surface, and wherein said second pyrocarbon articulating surfaces are positioned flush with said second articular surface.

3. The prosthetic device of claim 1, wherein said first pyrocarbon articulating surfaces are positioned proud of said first prosthetic component articulating surface, and wherein said second pyrocarbon articulating surfaces are positioned proud of said second articular surface.

4. The prosthetic device of claim 1, wherein each of the first and second plurality of pyrocarbon inserts comprise an attachment arrangement, the first and second plurality of pyrocarbon inserts arranged to be molded in place in the respective articulating and articular surface materials such that the respective materials engage the attachment arrangements to secure the first and second plurality of pyrocarbon inserts to the respective articulating and articular surface materials.

5. The prosthetic device of claim 4, wherein the articulating and articular surface materials each comprise a polymer material.

6. The prosthetic device of claim 4 wherein the articulating and articular surface materials each comprise a metallic material.

7. The prosthetic device of claim 4, wherein the attachment arrangement includes an annular recess positioned in a sidewall of each of the first and second plurality of pyrocarbon inserts.

8. The prosthetic device of claim 4, wherein each of the first and second plurality of pyrocarbon inserts includes a bottom surface opposite its articulating surface, and wherein the attachment arrangement includes at least one of an under cut formed in the bottom surface and a projection extending from the bottom surface.

9. The prosthetic device of claim 1, wherein the first and second prosthetic components comprise a first plurality and a second plurality of recesses in the respective articulating and articular surface materials, the first and second plurality of recesses configured to receive the respective first and second plurality of pyrocarbon inserts, the first and second plurality of pyrocarbon inserts being secured to the respective recesses with an adhesive.

10. The prosthetic device of claim 1, wherein each of the first plurality of pyrocarbon inserts is positioned in the articulating surface of the first prosthetic component such that the first longitudinal axis is parallel to and aligned with the second longitudinal axis of a respective one of the second plurality of pyrocarbon inserts positioned in the articular surface of the second prosthetic component.

11. The prosthetic device of claim 1, wherein each of the first and second plurality of pyrocarbon inserts comprises attachment means for securing the first and second plurality of pyrocarbon inserts to the respective articulating and articular surface materials.

12. An orthopedic prosthetic device, comprising:
a first and a second plurality of pyrocarbon inserts each having a first pyrocarbon articulating surface and an elongated body defining a first longitudinal axis;
a third and a fourth plurality of pyrocarbon inserts each having a second pyrocarbon articulating surface and an elongated body defining a second longitudinal axis;
a femoral prosthetic component having a bone engaging surface and medial and lateral condyle articulating surfaces, said medial and lateral condyle articulating surfaces being formed of a material distinct from pyrocarbon and arranged to receive the respective first and second plurality of pyrocarbon inserts so as to position the first pyrocarbon articulating surfaces relative to the respective medial and lateral condyle articulating surfaces; and
a tibial prosthetic component having a bone engaging surface and medial and lateral condyle articular surfaces that are formed from a material distinct from pyrocarbon and arranged to receive the respective third and fourth plurality of pyrocarbon inserts so as to position the second pyrocarbon articulating surfaces relative to the respective medial and lateral condyle articular surfaces;
wherein the femoral and tibial prosthetic components comprise a direction of articulation along which the first and second pyrocarbon articulating surfaces are configured to cooperate with each other, the first longitudinal axis of the first and second plurality of pyrocarbon inserts being parallel to the direction of articulation and the second longitudinal axis of the third and fourth plurality of pyrocarbon inserts being parallel to the direction of articulation, each of the first and second plurality of pyrocarbon inserts being aligned with a respective one of each of the third and fourth plurality of pyrocarbon inserts.

13. The prosthetic device of claim 12, wherein the first and second plurality of pyrocarbon inserts are molded or cast into place in the femoral prosthetic component articulating surface, and the third and fourth plurality of pyrocarbon inserts are molded or cast into place in the tibial prosthetic component articular surface.

14. The prosthetic device of claim 12, wherein each of the first and second plurality of pyrocarbon inserts are spaced apart from each other in the respective medial and lateral condyle articulating surfaces, and wherein each of the third and fourth plurality of pyrocarbon inserts are spaced part from each other in the respective medial and lateral condyle articular surfaces.

15. The prosthetic device of claim 12, wherein the first longitudinal axis of each of the first and second plurality of pyrocarbon inserts is parallel to and aligned with the second longitudinal axis of a respective one of the third and fourth plurality of pyrocarbon inserts.

16. The prosthetic device of claim 12, wherein the first pyrocarbon articulating surface of each of the first and second plurality of pyrocarbon inserts is positioned proud of the respective medial and lateral condyle articulating surfaces, and wherein the second pyrocarbon articulating surface of each of the third and fourth plurality of pyrocarbon inserts is positioned proud of the respective medial and lateral condyle articular surfaces.

17. The prosthetic device of claim 12, wherein the first pyrocarbon articulating surface of each of the first and second plurality of pyrocarbon inserts is positioned flush with the respective medial and lateral condyle articulating surfaces, and wherein the second pyrocarbon articulating surface of each of the third and fourth plurality of pyrocarbon inserts is positioned proud of the respective medial and lateral condyle articular surfaces.

18. The prosthetic device of claim 12, wherein the first pyrocarbon articulating surface of each of the first and second plurality of pyrocarbon inserts is positioned proud of the respective medial and lateral condyle articulating surfaces, and wherein the second pyrocarbon articulating surface of each of the third and fourth plurality of pyrocarbon inserts is positioned flush with the respective medial and lateral condyle articular surfaces.

19. An orthopedic prosthetic device, comprising:
a first and a second plurality of pyrocarbon inserts each having a first pyrocarbon articulating surface and an elongated body defining a first longitudinal axis;
a third and a fourth plurality of pyrocarbon inserts each having a second pyrocarbon articulating surface and an elongated body defining a second longitudinal axis;
a femoral prosthetic component having a bone engaging surface and medial and lateral condyle articulating surfaces, the medial and lateral condyle articulating surfaces being formed of a material distinct from pyrocarbon and arranged to receive each of the respective first and second plurality of pyrocarbon inserts in spaced relation to each other such that the medial and lateral condyle articulating surfaces surround each of the respective first and second plurality of pyrocarbon inserts; and
a tibial prosthetic component having a bone engaging surface and medial and lateral condyle articular surfaces, the medial and lateral condyle articular surfaces being formed from a material distinct from pyrocarbon and arranged to receive each of the respective third and fourth plurality of pyrocarbon inserts in spaced relation to each other such that the medial and lateral condyle articular surfaces surround each of the respective third and fourth plurality of pyrocarbon inserts;
wherein the femoral and tibial prosthetic components comprise a direction of articulation along which the first and second pyrocarbon articulating surfaces are configured to cooperate with each other, the first longitudinal axis of the first and second plurality of pyrocarbon inserts being parallel to the direction of articulation and the second longitudinal axis of the third and fourth plurality of pyrocarbon inserts being parallel to the direction of articulation, each of the first and second plurality of pyrocarbon inserts being aligned with a respective one of the third and fourth plurality of pyrocarbon inserts.

20. The prosthetic device of claim 19, wherein the first pyrocarbon articulating surface of each of the first and second plurality of pyrocarbon inserts is positioned proud of the respective medial and lateral condyle articulating surfaces, and wherein the second pyrocarbon articulating surface of each of the third and fourth plurality of pyrocarbon inserts is positioned proud of the respective medial and lateral condyle articular surfaces.

21. The prosthetic device of claim 19, wherein the first pyrocarbon articulating surface of each of the first and second plurality of pyrocarbon inserts is positioned flush with the respective medial and lateral condyle articulating surfaces, and wherein the second pyrocarbon articulating surface of each of the third and fourth plurality of pyrocarbon inserts is positioned proud of the respective medial and lateral condyle articular surfaces.

22. The prosthetic device of claim 19, wherein the first longitudinal axis of each of the first and second plurality of pyrocarbon inserts is parallel to and aligned with the second longitudinal axis of a respective one of the respective third and fourth plurality of pyrocarbon inserts.

\* \* \* \* \*